(12) United States Patent
Gorzitze

(10) Patent No.: US 10,231,697 B2
(45) Date of Patent: Mar. 19, 2019

(54) NEEDLE GUIDES FOR A SONOGRAPHIC IMAGING DEVICE

(71) Applicant: C. R. Bard, Inc., Murray Hill, NJ (US)

(72) Inventor: Jonathan C. Gorzitze, Kaysville, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 749 days.

(21) Appl. No.: 13/886,196

(22) Filed: May 2, 2013

(65) Prior Publication Data

US 2013/0245452 A1 Sep. 19, 2013

Related U.S. Application Data

(62) Division of application No. 12/642,456, filed on Dec. 18, 2009, now Pat. No. 8,574,160.

(60) Provisional application No. 61/138,606, filed on Dec. 18, 2008.

(51) Int. Cl.
   *A61B 8/00* (2006.01)
   *A61B 8/08* (2006.01)
   *A61B 17/34* (2006.01)
   *A61M 5/32* (2006.01)
   *A61M 5/42* (2006.01)

(52) U.S. Cl.
   CPC .......... *A61B 8/0841* (2013.01); *A61B 8/0833* (2013.01); *A61B 17/3403* (2013.01); *A61M 5/3287* (2013.01); *A61M 5/427* (2013.01); *A61B 2017/3411* (2013.01); *A61B 2017/3413* (2013.01)

(58) Field of Classification Search
   CPC ....... A61B 17/3403; A61B 2017/3413; A61M 5/427

USPC .......................... 600/641, 646, 459; 606/130
See application file for complete search history.

(56) References Cited

U.S. PATENT DOCUMENTS

| | | | |
|---|---|---|---|
| 2,470,488 | A | 5/1949 | Honerkamp et al. |
| 4,058,114 | A | 11/1977 | Soldner |
| 4,108,165 | A | 8/1978 | Kopp et al. |
| 4,341,303 | A | 7/1982 | Britt |

(Continued)

FOREIGN PATENT DOCUMENTS

| | | |
|---|---|---|
| CN | 3655315 | 6/2007 |
| DE | 2942405 A1 | 4/1981 |

(Continued)

OTHER PUBLICATIONS

PCT/US2009/068828 filed Dec. 18, 2009 International Preliminary Report on Patentability dated Jun. 21, 2011.

(Continued)

*Primary Examiner* — Rajeev Siripurapu
(74) *Attorney, Agent, or Firm* — Rutan & Tucker, LLP

(57) ABSTRACT

An medical device guide system includes a probe configured for imaging portions of a patient's body, a first guide connector extending from a first surface of the probe, the first guide connector including a first mounting surface, and a guide removably mountable to the first guide connector. The guide may include a first cavity shaped to receive the first mounting surface and a first channel disposed on a top surface of the guide opposite the first cavity, the first channel angled at a first angle with respect to a longitudinal axis of the probe and configured to guide a medical device to a targeted depth in the patient's body.

1 Claim, 14 Drawing Sheets

(56) References Cited

U.S. PATENT DOCUMENTS

| | | |
|---|---|---|
| 4,346,717 A | 8/1982 | Haerten |
| 4,363,326 A | 12/1982 | Kopel |
| 4,402,324 A | 9/1983 | Lindgren et al. |
| 4,408,611 A | 10/1983 | Enjoji |
| 4,469,106 A | 9/1984 | Harui |
| 4,497,325 A | 2/1985 | Wedel |
| 4,548,210 A | 10/1985 | Enjoji et al. |
| 4,576,175 A | 3/1986 | Epstein |
| 4,582,326 A | 4/1986 | Alsip |
| 4,608,989 A | 9/1986 | Drue |
| 4,635,644 A | 1/1987 | Yagata |
| 4,662,870 A | 5/1987 | Augustine et al. |
| 4,681,103 A | 7/1987 | Boner et al. |
| 4,723,544 A | 2/1988 | Moore et al. |
| 4,742,829 A | 5/1988 | Law et al. |
| 4,838,506 A | 6/1989 | Cooper |
| 4,877,033 A | 10/1989 | Seitz, Jr. |
| 4,883,059 A | 11/1989 | Stedman et al. |
| 4,898,178 A | 2/1990 | Wedel |
| 4,899,756 A | 2/1990 | Sonek |
| 4,911,173 A | 3/1990 | Terwilliger |
| 5,052,396 A | 10/1991 | Wedel et al. |
| 5,076,279 A | 12/1991 | Arenson et al. |
| 5,100,387 A | 3/1992 | Ng |
| 5,138,748 A | 8/1992 | Welles |
| 5,235,987 A * | 8/1993 | Wolfe ................. 600/461 |
| 5,265,614 A | 11/1993 | Hayakawa et al. |
| 5,280,427 A | 1/1994 | Magnusson et al. |
| 5,427,108 A | 6/1995 | Bollinger |
| D362,064 S | 9/1995 | Smick |
| 5,494,039 A | 2/1996 | Onik et al. |
| 5,623,931 A | 4/1997 | Wung et al. |
| 5,758,650 A * | 6/1998 | Miller et al. ................ 600/461 |
| D399,971 S | 10/1998 | Scherer |
| 5,911,707 A | 6/1999 | Wolvek et al. |
| D412,032 S | 7/1999 | Mikula-Curtis et al. |
| 5,924,992 A | 7/1999 | Park et al. |
| 5,941,889 A | 8/1999 | Cermak |
| 6,050,954 A | 4/2000 | Mittermeier |
| D424,693 S | 5/2000 | Pruter |
| 6,083,169 A | 7/2000 | Hansen |
| 6,095,981 A | 8/2000 | McGahan |
| D434,850 S | 12/2000 | Balestracci |
| 6,203,499 B1 | 3/2001 | Imling et al. |
| 6,283,942 B1 | 9/2001 | Staehlin et al. |
| 6,296,614 B1 | 10/2001 | Pruter |
| 6,361,499 B1 | 3/2002 | Bates et al. |
| 6,368,280 B1 | 4/2002 | Cermak et al. |
| 6,379,307 B1 | 4/2002 | Filly et al. |
| 6,425,871 B1 | 7/2002 | Jaggi |
| 6,475,152 B1 | 11/2002 | Kelly, Jr. et al. |
| 6,485,426 B2 | 11/2002 | Sandhu |
| 6,612,990 B1 | 9/2003 | Pruter |
| 6,695,786 B2 | 2/2004 | Wang et al. |
| 6,743,177 B2 | 6/2004 | Ito et al. |
| 6,758,817 B1 | 7/2004 | Pruter et al. |
| 6,814,704 B2 | 11/2004 | Weilandt |
| 6,840,954 B2 | 1/2005 | Dietz et al. |
| 6,877,352 B1 | 4/2005 | Schlereth |
| 6,884,219 B1 | 4/2005 | Pruter |
| 6,908,433 B1 | 6/2005 | Pruter |
| 7,022,082 B2 | 4/2006 | Sonek |
| 7,087,024 B1 | 8/2006 | Pruter |
| 7,322,990 B1 | 1/2008 | Mark et al. |
| 7,351,205 B2 | 4/2008 | Szczech et al. |
| 7,452,331 B1 | 11/2008 | Pruter |
| 7,588,541 B2 | 9/2009 | Floyd et al. |
| 7,635,336 B1 | 12/2009 | Pruter |
| 7,670,294 B2 | 3/2010 | Kisen et al. |
| 7,691,066 B2 | 4/2010 | Kosaku |
| D625,802 S | 10/2010 | Choi et al. |
| D625,805 S | 10/2010 | Hereford |
| 7,837,627 B1 | 11/2010 | Pruter |
| D629,898 S | 12/2010 | Bigelow |
| D630,731 S | 1/2011 | Schmutzer et al. |
| 7,909,815 B2 | 3/2011 | Whitmore, III et al. |
| 7,976,469 B2 | 7/2011 | Bonde et al. |
| D649,245 S | 11/2011 | Klebs et al. |
| 8,073,529 B2 | 12/2011 | Cermak et al. |
| 8,075,495 B2 | 12/2011 | Andreyko et al. |
| 8,118,743 B2 | 2/2012 | Park et al. |
| D655,813 S | 3/2012 | Row et al. |
| 8,137,281 B2 | 3/2012 | Huang et al. |
| D659,825 S | 5/2012 | Dillard, III |
| D672,460 S | 12/2012 | Baid |
| 8,430,889 B2 | 4/2013 | Zeng et al. |
| D683,019 S | 5/2013 | Shahidi Bonjar |
| 8,496,593 B2 | 7/2013 | Park et al. |
| 8,523,824 B2 | 9/2013 | Teirstein et al. |
| 8,641,620 B2 | 2/2014 | Lasser et al. |
| 8,647,280 B2 | 2/2014 | Ooishi et al. |
| 8,696,583 B2 | 4/2014 | Ohgishi et al. |
| 8,696,585 B2 | 4/2014 | Addison et al. |
| 8,708,916 B2 | 4/2014 | Okuno |
| 8,740,800 B2 | 6/2014 | Wakabayashi et al. |
| 8,747,324 B1 | 6/2014 | Pruter et al. |
| D710,995 S | 8/2014 | Shirley et al. |
| 8,795,183 B2 | 8/2014 | Siebrecht et al. |
| 8,808,186 B2 | 8/2014 | Fruland et al. |
| D727,495 S | 4/2015 | Bown et al. |
| 9,788,812 B2 | 10/2017 | Orome et al. |
| 2002/0123689 A1 | 9/2002 | Furia |
| 2002/0133079 A1 | 9/2002 | Sandhu |
| 2003/0144627 A1 | 7/2003 | Woehr et al. |
| 2003/0195425 A1 | 10/2003 | Ito |
| 2004/0133111 A1 | 7/2004 | Szczech et al. |
| 2005/0059891 A1 | 3/2005 | Kosaku |
| 2005/0113816 A1 | 5/2005 | Whitmore et al. |
| 2005/0143753 A1 | 6/2005 | Whitmore et al. |
| 2005/0267373 A1 | 12/2005 | Lee |
| 2006/0129046 A1 | 6/2006 | Stevens et al. |
| 2006/0150876 A1 | 7/2006 | Green et al. |
| 2006/0241477 A1 | 10/2006 | Sasady et al. |
| 2007/0016781 A1 | 1/2007 | Asokan et al. |
| 2007/0038113 A1 | 2/2007 | Oonuki et al. |
| 2007/0073155 A1 | 3/2007 | Park et al. |
| 2007/0078346 A1 | 4/2007 | Park et al. |
| 2007/0112272 A1 | 5/2007 | Park et al. |
| 2007/0167817 A1 * | 7/2007 | Huang et al. ................. 600/461 |
| 2007/0276241 A1 | 11/2007 | Park et al. |
| 2007/0276253 A1 * | 11/2007 | Park et al. ................... 600/461 |
| 2007/0282205 A1 | 12/2007 | Furia |
| 2008/0033454 A1 | 2/2008 | Lukoschek et al. |
| 2008/0300491 A1 | 12/2008 | Bonde et al. |
| 2009/0143684 A1 | 6/2009 | Cermak et al. |
| 2009/0171219 A1 | 7/2009 | Uchibori |
| 2009/0247876 A1 | 10/2009 | Cannon, Jr. et al. |
| 2009/0266957 A1 * | 10/2009 | Cermak ................. 248/225.11 |
| 2009/0270722 A1 | 10/2009 | Floyd et al. |
| 2009/0275833 A1 * | 11/2009 | Ikeda et al. ................... 600/443 |
| 2010/0010475 A1 | 1/2010 | Teirstein et al. |
| 2010/0041990 A1 | 2/2010 | Schlitt et al. |
| 2010/0081920 A1 | 4/2010 | Whitmore, III et al. |
| 2010/0106056 A1 | 4/2010 | Norris |
| 2010/0160787 A1 | 6/2010 | Gorzitze |
| 2010/0228131 A1 | 9/2010 | Oonuki et al. |
| 2010/0247513 A1 | 9/2010 | Agee et al. |
| 2010/0312121 A1 | 12/2010 | Guan |
| 2011/0028847 A1 | 2/2011 | Whitmore, III et al. |
| 2012/0165679 A1 | 6/2012 | Orome et al. |
| 2012/0330159 A1 | 12/2012 | Orome et al. |
| 2013/0150714 A1 | 6/2013 | Howlett et al. |
| 2015/0025315 A1 | 1/2015 | Nishina et al. |
| 2015/0112200 A1 | 4/2015 | Oberg et al. |

FOREIGN PATENT DOCUMENTS

| | | |
|---|---|---|
| EP | 1709919 A1 | 10/2006 |
| JP | 01097440 A | 4/1989 |
| JP | 03173542 A | 7/1991 |
| JP | 11128237 A | 5/1999 |
| JP | 21161683 | 6/2001 |
| JP | 21340334 | 12/2001 |
| JP | 23299654 | 10/2003 |

(56) References Cited

FOREIGN PATENT DOCUMENTS

| | | |
|---|---|---|
| JP | 23334191 | 11/2003 |
| JP | 2005-034273 A | 2/2005 |
| JP | D1268564 | 4/2006 |
| JP | 2009-153831 A | 7/2009 |
| JP | 2010-115246 A | 5/2010 |
| WO | 1996010958 A2 | 4/1996 |
| WO | 2000019906 | 4/2000 |
| WO | 2000040155 A1 | 7/2000 |
| WO | 2003094701 A2 | 11/2003 |
| WO | 2004021898 A1 | 3/2004 |
| WO | 2006060657 A2 | 6/2006 |
| WO | 2007027511 A2 | 3/2007 |
| WO | WO 2007040172 A1 * | 4/2007 |
| WO | 2007110076 A1 | 10/2007 |
| WO | 2008024515 A2 | 2/2008 |
| WO | 2009073653 A1 | 6/2009 |
| WO | 2009090230 A1 | 7/2009 |
| WO | 2010080637 A1 | 7/2010 |
| WO | 2010084322 A1 | 7/2010 |
| WO | 2012088458 | 6/2012 |
| WO | 2012178109 | 12/2012 |
| WO | 2013054168 A2 | 4/2013 |
| WO | 2015100332 A1 | 7/2015 |

OTHER PUBLICATIONS

PCT/US2009/068828 filed Dec. 18, 2009 Search Report dated Mar. 3, 2010.
PCT/US2009/068828 filed Dec. 18, 2009 Written Opinion dated Mar. 3, 2010.
U.S. Appl. No. 12/642,456, filed Dec. 18, 2009 Final Office Action dated Nov. 23, 2012.
U.S. Appl. No. 12/642,456, filed Dec. 18, 2009 Non-Final Office Action dated Jul. 2, 2012.
PCT/US2011/066940 filed Dec. 22, 2011 International Preliminary Report on Patentability dated Jul. 4, 2013.
PCT/US2011/066940 filed Dec. 22, 2011 International Search Report and Written Opinion dated Apr. 20, 2012.
PCT/US2012/043877 filed Jun. 22, 2012 International Search Report and Written Opinion dated Sep. 24, 2012.
U.S. Appl. No. 12/642,456, filed Dec. 18, 2009 Notice of Allowance dated Jul. 12, 2013.
U.S. Appl. No. 13/335,587, filed Dec. 22, 2011 Non-Final Office Action dated Mar. 12, 2014.
U.S. Appl. No. 13/335,587, filed Dec. 22, 2011 Final Office Action dated Jul. 28, 2014.
EP 14875859.2 filed Jun. 9, 2016 Extended European Search Report dated Jul. 31, 2017.
JP 2014-517229 filed Dec. 20, 2013 First Office Action dated May 24, 2016.
U.S. Appl. No. 13/531,406, filed Jun. 22, 2012 Non-Final Office Action dated Aug. 10, 2016.
CN 201180067467.2 filed Aug. 13, 2013 First Office Action dated Sep. 4, 2014.
CN 201180067467.2 filed Aug. 13, 2013 second Office Action dated Apr. 30, 2015.
CN 201180067467.2 filed Aug. 13, 2013 Third Office Action dated Oct. 28, 2015.
CN 201280030885.9 filed Dec. 23, 2013 First Office Action dated Mar. 3, 2015.
EP 11 850 516.3 filed Jul. 19, 2013 Extended European Search Report dated Mar. 4, 2015.
EP 12 803 493.1 filed Jan. 15, 2014 Extended European Search Report dated Mar. 5, 2015.
PCT/US2014/072168 filed Dec. 23, 2014 International Search Report and Written Opinion dated Apr. 16, 2015.
U.S. Appl. No. 13/335,587, filed Dec. 22, 2011 Final Office Action dated Jul. 8, 2015.
U.S. Appl. No. 13/335,587, filed Dec. 22, 2011 Non-Final Office Action dated Feb. 2, 2015.
U.S. Appl. No. 13/531,406, filed Jun. 22, 2012 Non-Final Office Action dated Aug. 18, 2015.
U.S. Appl. No. 13/531,406, filed Jun. 22, 2012 Non-Final Office Action dated Jan. 9, 2015.
U.S. Appl. No. 29/493,150, filed Jun. 5, 2014 Notice of Allowance dated Oct. 29, 2015.
CN 201280030885.9 filed Dec. 23, 2013 Second Office Action dated Nov. 4, 2015.
CN 201280030885.9 filed Dec. 23, 2013 Third Office Action dated May 5, 2016.
U.S. Appl. No. 13/335,587, filed Dec. 22, 2011 Examiner's Answer dated May 16, 2016.
U.S. Appl. No. 13/531,406, filed Jun. 22, 2012 Advisory Action dated May 3, 2017.
U.S. Appl. No. 13/531,406, filed Jun. 22, 2012 Final Office Action dated Feb. 27, 2017.
U.S. Appl. No. 14/581,019, filed Dec. 23, 2014 Non-Final Office Action dated Apr. 12, 2017.
U.S. Appl. No. 13/531,406, filed Jun. 22, 2012 Final Office Action dated Feb. 25, 2016.

* cited by examiner

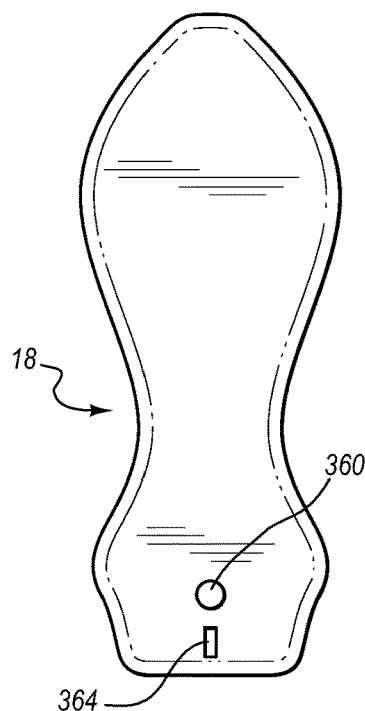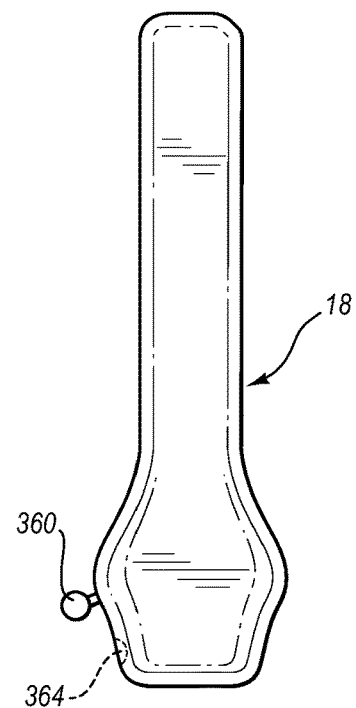
FIG. 5A  FIG. 5B
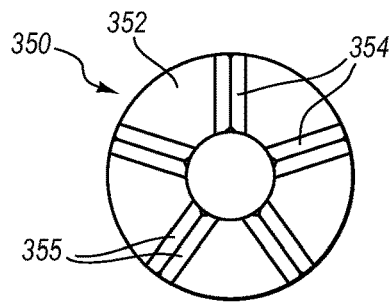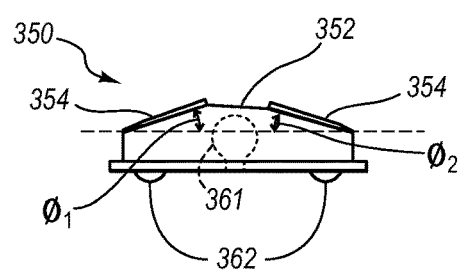
FIG. 6A  FIG. 6B
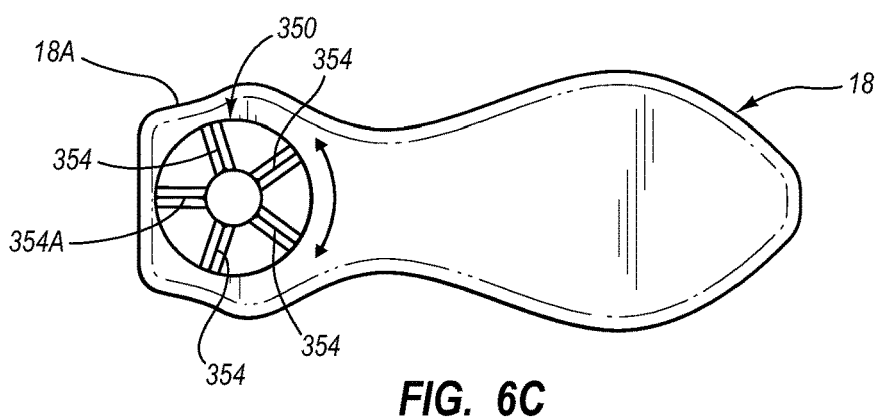
FIG. 6C

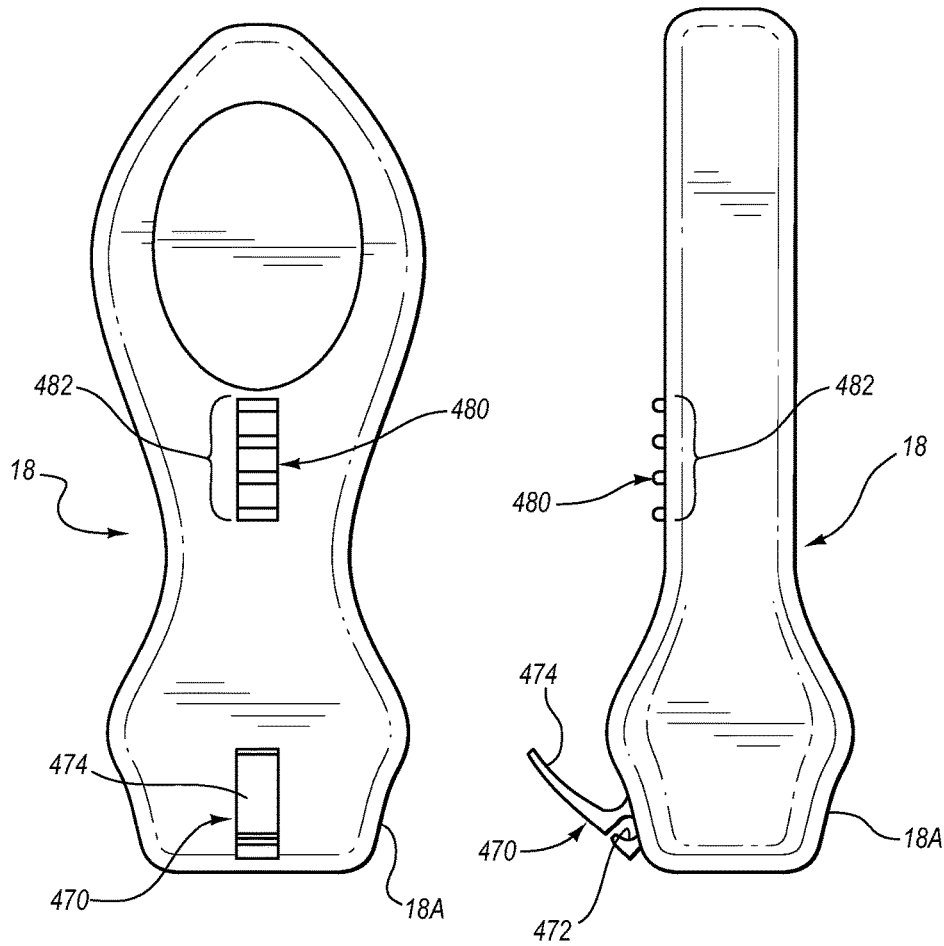
FIG. 7A  FIG. 7B

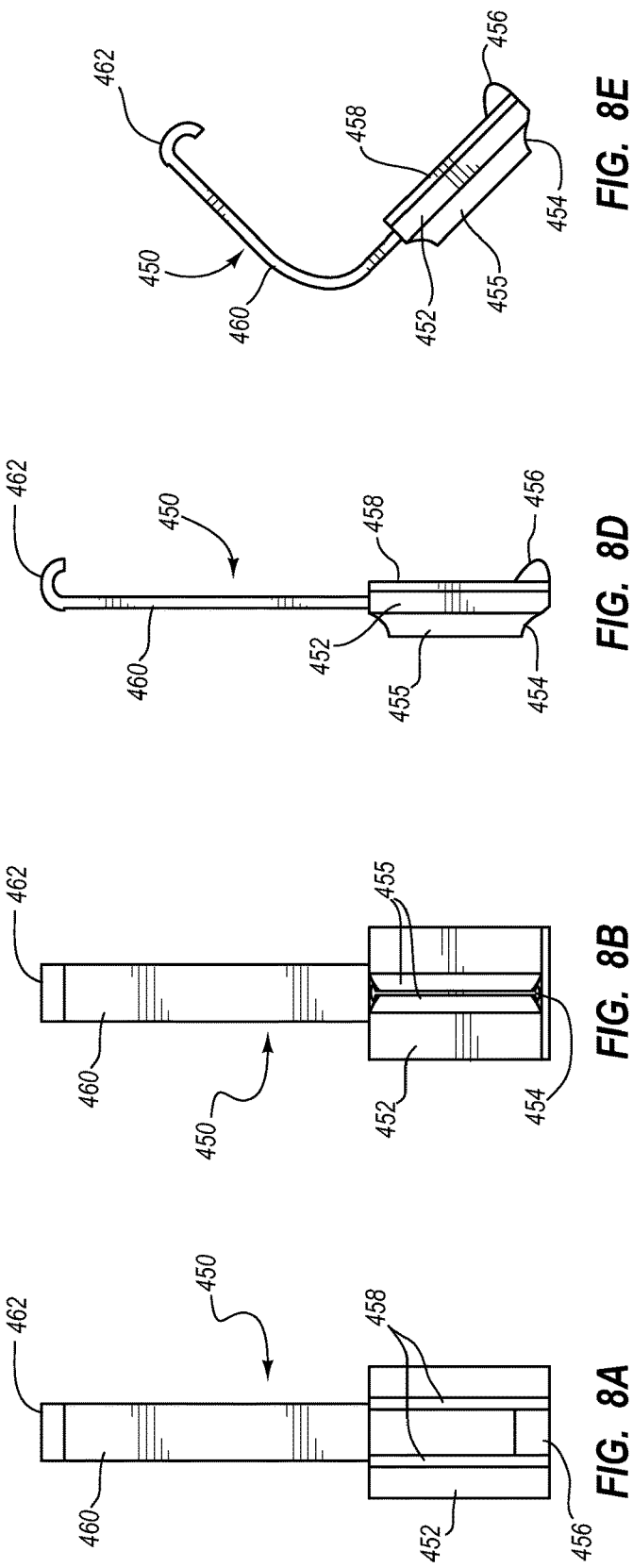

NEEDLE GUIDES FOR A SONOGRAPHIC IMAGING DEVICE

CROSS-REFERENCE TO RELATED APPLICATIONS

This application is a division of U.S. patent application Ser. No. 12/642,456, filed Dec. 18, 2009, now U.S. Pat. No. 8,574,160, which claims the benefit of U.S. Provisional Patent Application No. 61/138,606, filed Dec. 18, 2008, each of which is incorporated herein by reference in its entirety.

BRIEF SUMMARY

Briefly summarized, embodiments of the present invention are directed to needle guide systems for a sonography device. The needle guide systems include both fixed and adjustable needle guides for use with a probe of the sonography device.

In one embodiment, the needle guide includes a needle guide body that is rotatably mounted to a sonography device probe. A plurality of needle channels is disposed on a surface of the needle guide body. Each needle channel can be selectively rotated into position to guide a needle into a body of a patient at a predetermined needle insertion angle. If another needle insertion angle is desired, the needle guide is rotated to place a new needle channel defining the desired needle insertion angle into position. The needle guide can be permanently or removably attached to the probe.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIGS. 5A-6E are various views of an adjustable needle guide system according to one embodiment;

FIGS. 7A-8F are various views of an adjustable needle guide system according to another embodiment;

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a needle or catheter placed within the body of a patient is considered a distal end of the needle or catheter, while the needle or catheter end remaining outside the body is a proximal end of the needle or catheter. Also, the words "including," "has," and "having," as used herein, including the claims, shall have the same meaning as the word "comprising."

FIGS. 1-11D depict various features of embodiments of the present invention, which are generally directed to needle guide systems for use with a sonographic imaging device in assisting the percutaneous insertion of a needle or other medical device into a body portion, such as a vasculature of a patient, for instance.

Figure 1:
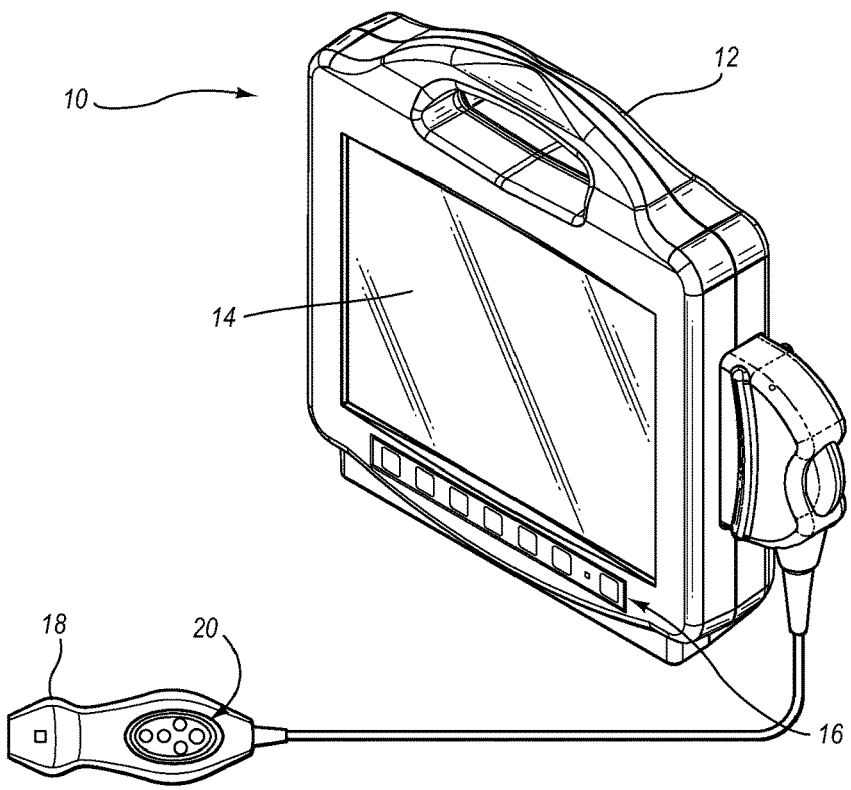
FIG. 1 is simplified perspective view of a sonographic imaging system that serves as an example environment in which embodiments of the present invention can be practiced.

Reference is first made to FIG. 1 in describing a sonographic imaging system ("system"), generally described at 10, for ultrasonically imaging portions of a patient body. The system 10 includes a console 12 including a display 14 and one or more user input controls 16. In one embodiment, the system 10 also includes a probe 18 including one or more user controls in the form of control buttons 20. Briefly, the probe 18 is configured to transmit ultrasonic signals from a head portion 18A thereof into a portion of a patient body and to receive the ultrasonic signals after reflection by internal structures of the patient body. The system 10 processes the reflected ultrasonic signals for depiction on the display 14.

The user input controls 16 of the console 12 may include, for example, image gain controls to adjust the amplification of a received ultrasonic signal, image depth controls to image structures at different depths and adjust the focus of an ultrasonic image displayed on the display 14, depth marker controls to selectively display depth markers and/or grid lines, print and/or save controls to print/save an image currently displayed on the display, image freeze controls to pause an image currently displayed on the display, time/date set controls, and other controls for operating the system 10. Corresponding controls, or a subset thereof, are also included in the control buttons 20 on the probe 18. In addition, in other embodiments the functionality of the user input controls 16 can be provided by a keyboard, mouse, or other suitable input device.

Figure 2:
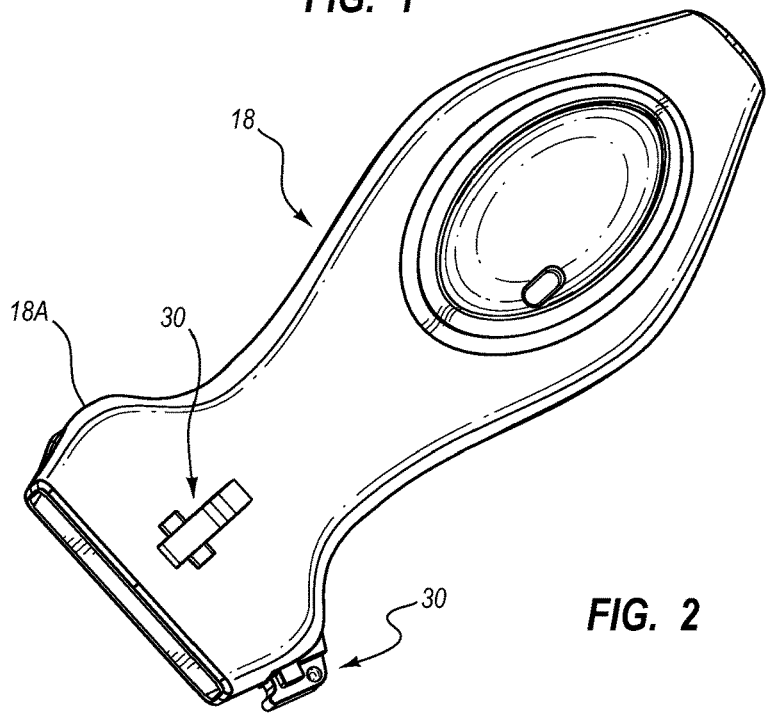
FIG. 2 is a perspective view of a handheld probe of the system of FIG. 1.

FIG. 2 shows the probe 18 of FIG. 1, including two needle guide connectors 30 that are included as part of a needle guide mounting system configured in accordance with one example embodiment. The needle guide connectors 30 are included on front and side portions of the probe 18 but are identically configured in the present embodiment. As such, the details of only one of the connectors will be described in detail here. It should be appreciated that in other embodiments the needle guide connectors may differ in size, configuration, the number included on the probe, etc. In addition, the design and configuration of the probe is merely one example of an ultrasonic probe that can benefit from the principles described herein.

Figure 3A:
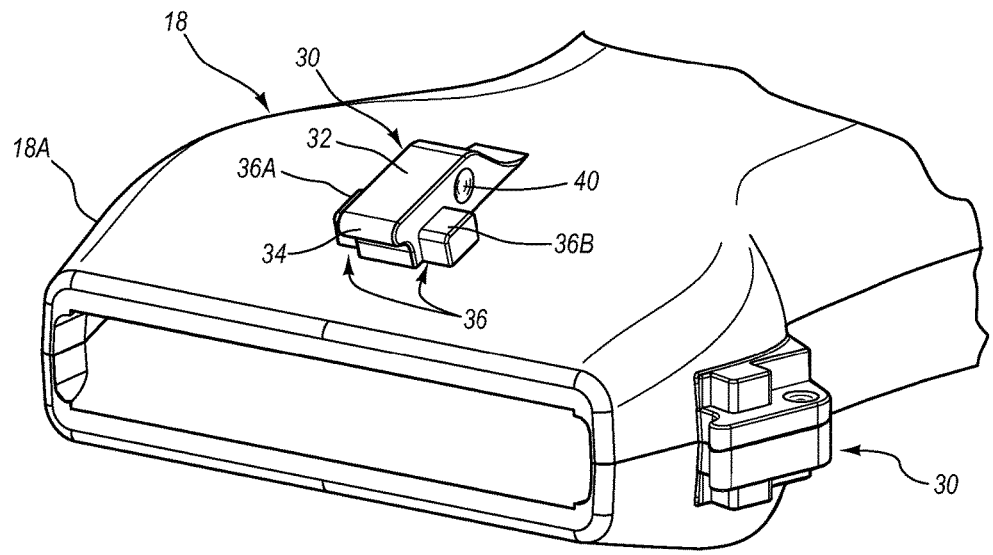
FIGS. 3A and 3B are various views of a portion of a needle guide system included on a handheld probe according to one example embodiment, included on the probe of FIG. 2.
Figure 3B:
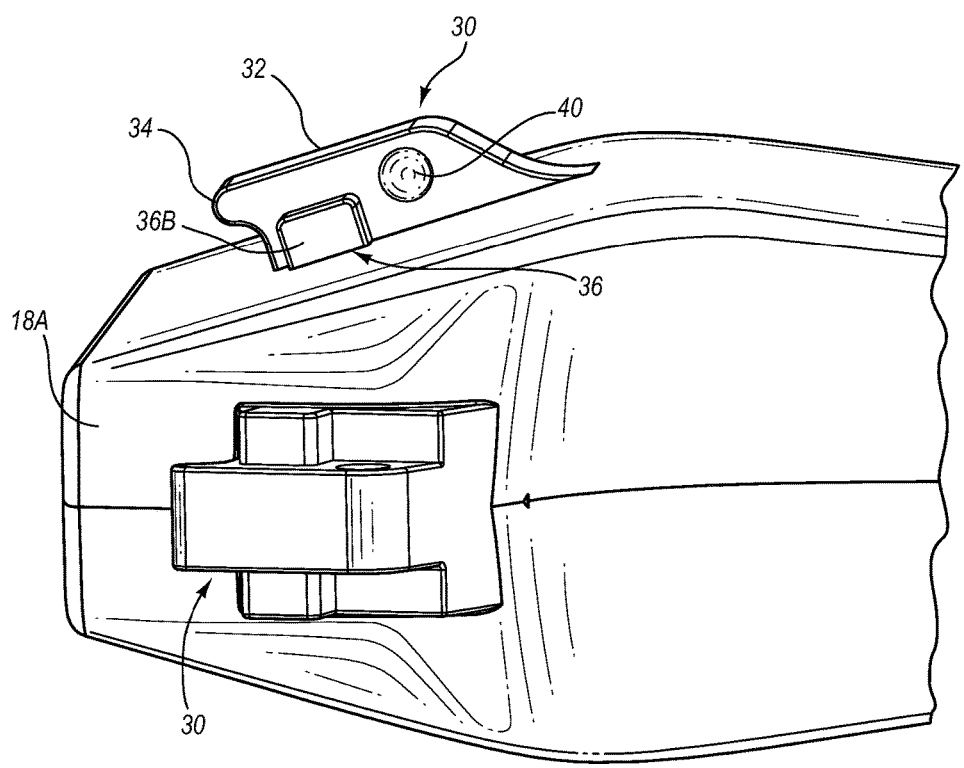

FIGS. 3A and 3B give further details of the needle guide connectors 30 according to one embodiment. Each connector 30 includes an elongate first mounting surface 32, extending from the surface of the probe head portion 18A, which is configured to receive a needle guide thereon, as will be described. An overhang 34 is defined at an end of the mounting surface 32 for assistance in maintaining engagement of the needle guide with the connector 30. A second mounting surface 36 is also included on the each connector 30, which surface defines two stability extensions 36A, 36B. In the present embodiment, the stability extensions 36A, 36B are integrally formed with the first mounting surface 32 and extend along an axis in a direction that is substantially orthogonal to a longitudinal axis of the first mounting surface. So configured, the second mounting surface 36, as defined by the stability extensions 36A and 36B, also extends substantially orthogonal to the first mounting surface 32, though in other embodiments the two mounting surfaces can be aligned at other angles with respect to one another. Note that the size, number, and orientation of the second mounting surface and its respective stability extensions with respect to the first mounting surface can vary from what is explicitly described herein.

One or more depressions 40 are defined on side surfaces of the first mounting surface 32 for engagement with corresponding protrusions defined on the needle guide, as will be described. Of course, other configurations for maintaining engagement between the needle guide and the mounting surfaces of the needle guide connector 30 can also be employed.

Reference is now made to FIGS. 4A-4D, which depict various details of a needle guide, generally designated at 50, in accordance with one example embodiment. As shown, the needle guide 50 includes a top surface 52 on which a needle channel 54, defined by two lips 55, is defined for guiding a needle to a body portion imaged by the system 10 via percutaneous insertion. The top surface 52, and therefore the needle channel 54, is angled with respect to a longitudinal axis of the probe 18 so as to enable the needle to intercept the targeted body portion at a depth as determined by the ultrasonic imaging performed by the system 10. The needle insertion angle defined by the needle channel 54 can vary according to the configuration of the needle guide. Thus, selection of an appropriately angled needle guide is determined by the depth of the intended subcutaneous target within the patient body to be intercepted. As such, the specific size and configuration details of the needle guide described herein are merely examples.

Figure 4A:
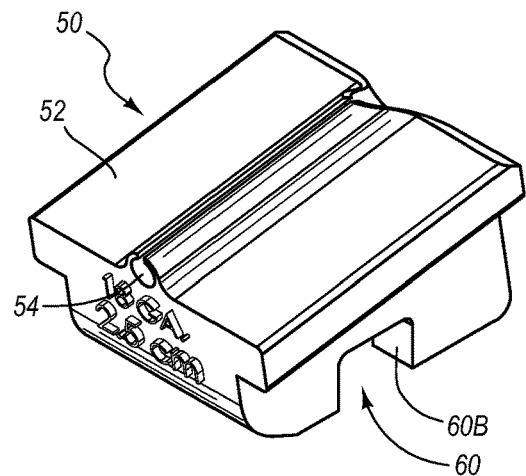
FIGS. 4A-4D are various views of a needle guide for use with the handheld probe shown in FIGS. 3A and 3B, according to one embodiment.
Figure 4B:
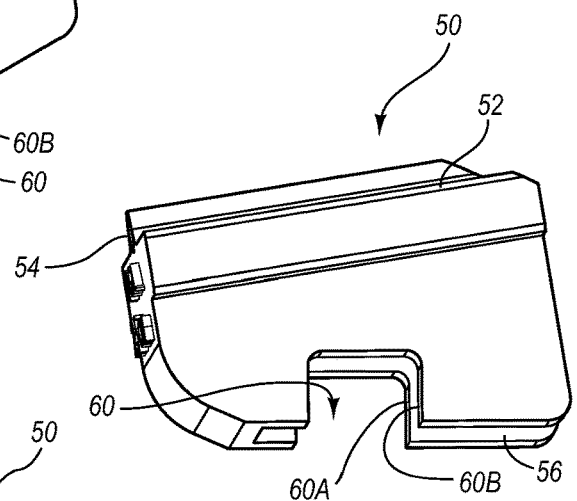
Figure 4C:
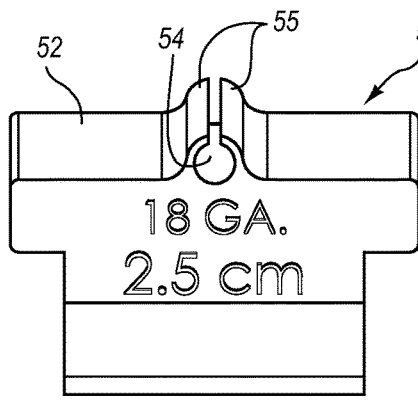
Figure 4D:
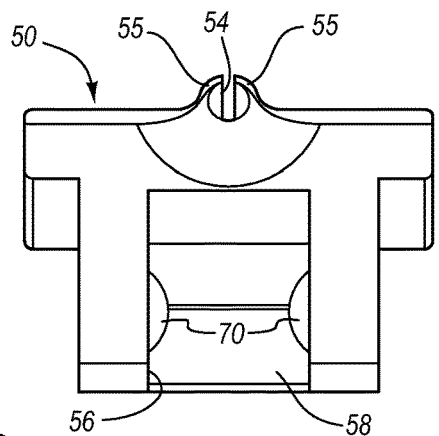

The needle guide 50 defines a first cavity 56, best seen in FIG. 4D, which is shaped to receive therein the first mounting surface 32 of the connector 30 when the needle guide is removably attached to the probe 18. A smoothly shaped extended surface 58 is included at the closed end of the cavity 56 and is configured for interfacing with the smoothly shaped overhang 34 of the first mounting surface 32 in retaining the needle guide 50 on the connector 30 when attached thereto. The extended surface 58 and overhang 34 can be configured in a variety of ways so as to assist in retaining the needle guide on the connector 30.

Figure 4E:
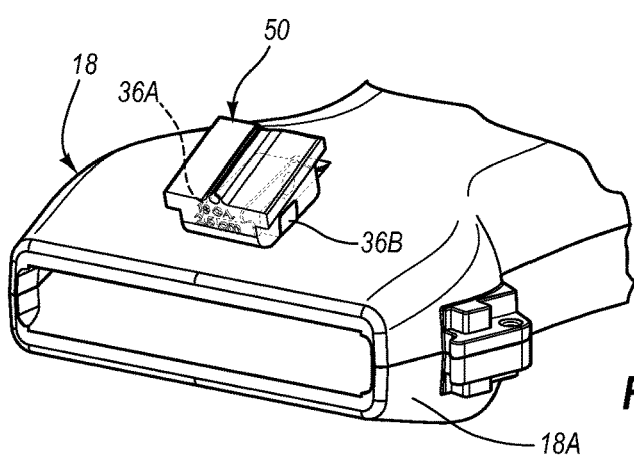
FIG. 4E is a perspective view of the needle guide of FIGS. 4A-4D attached to the probe of FIG. 2.

A second cavity 60, which crosses substantially orthogonally the first cavity 56 and includes notches 60A, 60B, is defined by the body of the needle guide 50, as best seen in FIG. 4B. The notches 60A, 60B of the second cavity 60 are positioned to respectively receive therein the stability extensions 36A, 36B when the needle guide 50 is attached to the needle guide connector 30, such as in a snap-fit configuration for instance, as shown in FIG.4E. So attached, the stability extensions 36A, 36B of the connector 30 engage the notches 60A, 60B and this engagement, together with the engagement of the first mounting surface 32 with the needle guide cavity 56, secures the needle guide in place with respect to the probe 18. This in turn provides a stable needle guide structure that resists undesired movement, such as the needle guide undesirably slipping off the probe in a direction parallel to a longitudinal axis of the probe 18. Thus, the needle guide remains in place to enable a clinician to insert a needle or other medical instrument into the target area of the patient body via the needle channel 54 while the target area is imaged by the sonography system 10. It is appreciated that the angle of intersection between the first cavity 56 and the second cavity 60 of the needle guide 50 should be configured to match the angle of intersection between the first mounting surface 32 and the second mounting surface 36 of the needle guide connector 30 of the probe 18 in all cases, regardless of whether the angle of intersection is orthogonal.

The needle guide 50 further includes protrusions 70 in the first cavity 56 that are sized and positioned to engage with the depressions 40 (FIGS. 3A, 3B) of the needle guide connector 30 when the needle guide is attached to the needle guide connector 30. Note that the size, shape, number, and other configuration details of the needle guide cavities can vary from what is described herein while still residing within the scope of present embodiments. For instance, the shape defined by the notches 60A, 60B, can be triangular, rounded, etc., instead of the square configuration shown here.

The needle channel 54 of FIGS. 4A-4E is shown to be sized for an 18 Gauge needle. In other embodiments, however, the needle channel can be sized to accommodate needles of other sizes and configurations. Also, the needle guide can be configured in one embodiment to accept devices other than needles, such as trocars or catheters for instance. As mentioned above, the needle guide top surface can be configured such that the needle channel defines an angle with a longitudinal axis of the probe 18 different from what is shown in FIGS. 4A-4E. As such, multiple needle guides, each having a needle channel defining a unique angle with the longitudinal axis of the probe 18, can be constructed as to be selectively attachable to/removable from the probe needle guide connector 30 of the probe 18, enabling a plurality of needle insertion angles to be achieved with the system 10.

Reference is now made to FIGS. 5A-6E in describing a needle guide system according to another embodiment. FIGS. 5A and 5B show the probe 18 including a mounting component, such as a mounting ball 360 (see also mounting ball 361 in FIGS. 6B, 6D, and 6E), on the probe head portion 18A for rotatably receiving a rotatable needle guide 350, shown in FIGS. 6A and 6B. As shown, the needle guide 350 includes a circular body that defines a chamfered or slanted top surface 352. A plurality of needle channels 354 is included on the top surface. Each needle channel 354 is defined by two lips 355 or other suitable structure. The top surface 352 is configured such that each needle channel 354 is positioned at a unique angle. For instance, FIG. 6B shows one needle channel 354 of the needle guide 350 angled to define a deflection angle $\phi_1$ with respect to horizontal and another needle channel 354 angled to define a deflection angle $\phi_2$ with respect to horizontal, from the perspective shown in FIG. 6B. As will be seen, this enables the needle guide to guide a needle into the patient body at one of a plurality of different needle insertion angles, measured with respect to a longitudinal axis of the probe 18 to which the needle guide is either removably or permanently attached. In the illustrated embodiment, five needle channels 354 are included on the top surface 352 of the needle guide 350, though more or fewer than this can be included. Also, though shown distributed in a star pattern, the distribution of the needle channels on the needle guide top surface can vary from what is shown and described herein.

Figure 6D:
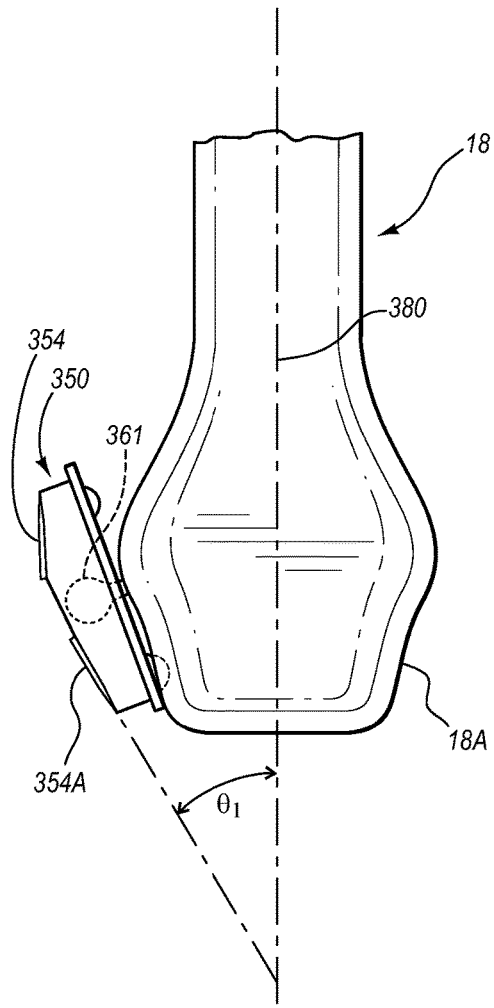

As mentioned, the needle guide 350 is configured to attach to a fixture on the probe 18, such as the mounting ball 360 shown in FIGS. 5A and 5B (see also mounting ball 361 in FIGS. 6B, 6D, and 6E) or other suitable structure, such that the needle guide 350 is rotatable with respect to the probe. The fixture can be placed on any suitable surface of the probe 18. One or more protrusions 362 are included on a bottom surface of the needle guide 350 and are each positioned so as to engage a depression 364 defined on the surface of the probe head portion 18A and thus secure the needle guide in a particular position until moved by a force sufficient to overcome the friction engagement between the corresponding protrusion and the depression. So configured, a clinician may rotate the needle guide 350, as shown in FIG. 6C, until the desired needle channel 354 having the desired insertion angle is aligned at a usable position 354A to enable the clinician to insert a correspondingly sized needle into the patient body via the selected needle channel to intercept an imaged target area of the patient body at a predetermined depth. Note that the location, number, and configuration of the protrusions and depressions can vary from what is shown and described.

Figure 6E:
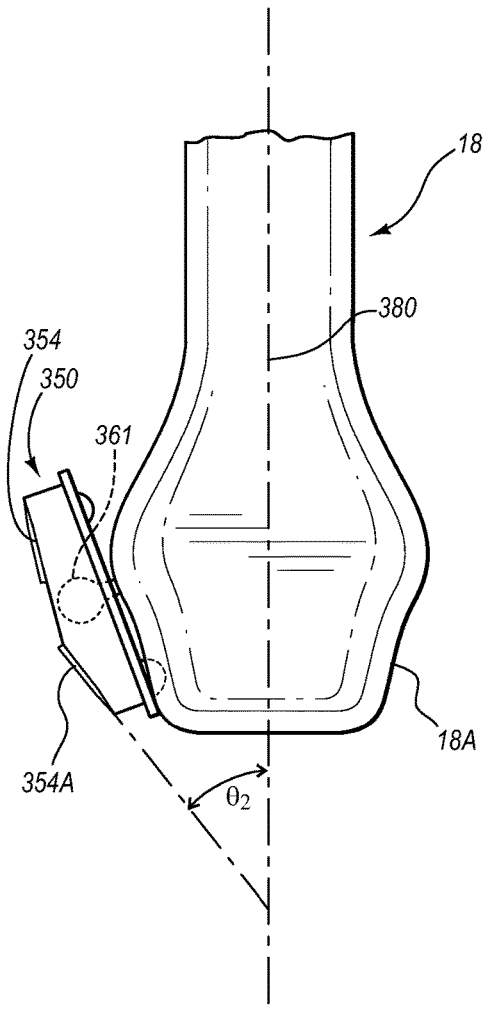

FIGS. 6D and 6E show how the needle guide 350 enables needle insertions of different angles of entry into the patient body. In FIG. 6D, one of the needle channels 354 is positioned for use, i.e., in the position 354A (see FIG. 6C) such that it defines a needle insertion angle $\theta_1$ with the longitudinal axis 380 of the probe 18. In contrast, FIG. 6E shows another needle guide channel 354 in the position 354A, which defines a needle insertion angle $\theta_2$ with the probe longitudinal axis 380. As can be seen from FIGS. 6D and 6E, the needle path enabled by the needle channel 354 of FIG. 6D penetrates more deeply relative to the needle path enabled by the needle channel 354 of FIG. 6E. As such, the needle channel 354 of FIG. 6D can be employed in order to enable a needle to intercept a target area of the patient body that is relatively deeper, while the needle channel shown in FIG. 6E can be employed to intercept a relatively shallower target area.

Thus, in accordance with the present embodiment, the needle guide 350 can be used to direct a needle to a proper depth within the patient body during use of the probe 18 and system 10. In particular, once a target area of the patient body has been located by the probe 18 and imaged by the system 10, the clinician rotates the needle guide 350 until a desired one of the needle channels 354 having a desired needle insertion angle with respect to the longitudinal axis 380 of the probe 18 is in the position 354A and ready for use. The clinician can then insert the needle into the needle channel 354, which channel guides the needle into the patient body at the desired needle insertion angle until the needle intercepts the target area.

Note that the shape and size of the needle guide can vary from what is described here. For instance, the general shape of the needle guide can be hexagonal, pentagonal, triangular, square, or other geometric shape in one embodiment. Also, the needle guide can be reduced in size from what is shown in FIGS. 6D and 6E in order to match a configuration of the sonographic probe. The needle channels can each be sized to accommodate needles of differing gauges in one embodiment.

Reference is now made to FIGS. 7A-8E in describing a needle guide system according to another embodiment. In particular, FIGS. 8A-8E show a needle guide 450, which generally includes a base 452 and a flexible extension 460. The base 452 includes on a top surface thereof a needle channel 454 defined by lips 455 and on a bottom surface a connector 456 for attaching the needle guide 450 to the probe 18 and longitudinally extending stability rails 458 for preventing twisting or torsion of the needle guide during use on the probe. The flexible extension 460 is an elongate member that longitudinally extends from the base 452 and includes a first engagement feature, such as a hook 462, at a free end 460A of the extension.

Figure 8F:
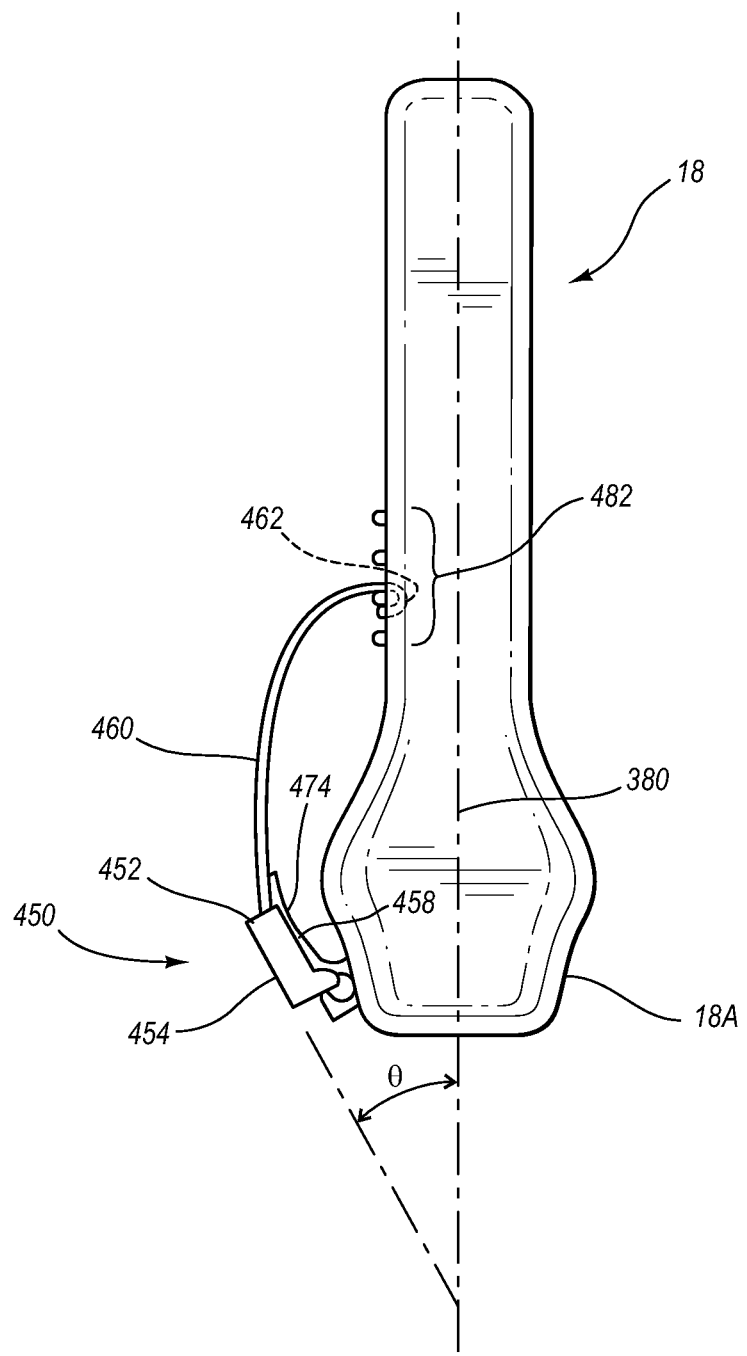
Figure 9A:
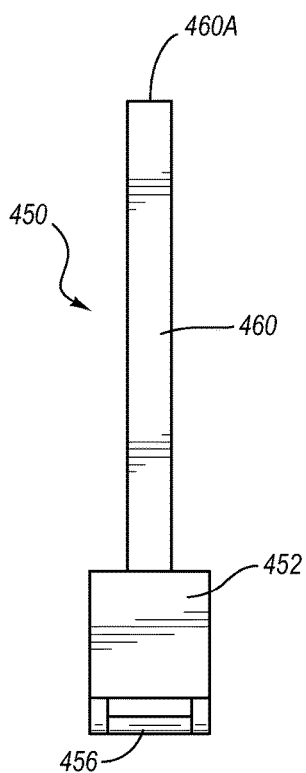
FIGS. 9A-10F are various views of an adjustable needle guide system according to yet another embodiment.
Figure 9B:
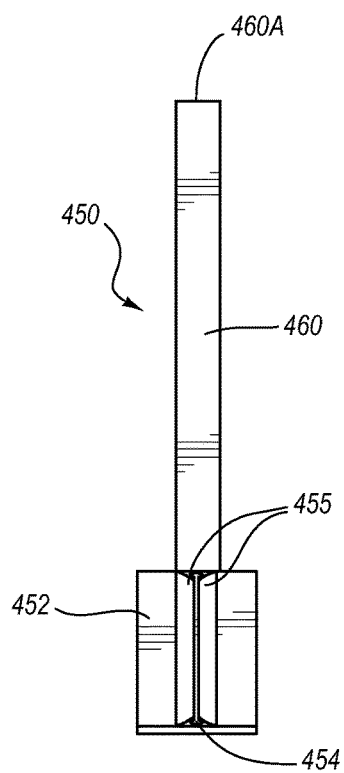
Figure 9C:
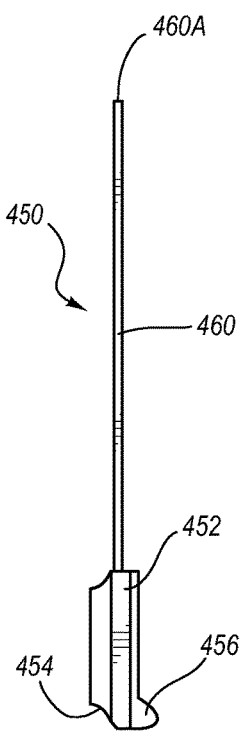
Figure 9D:
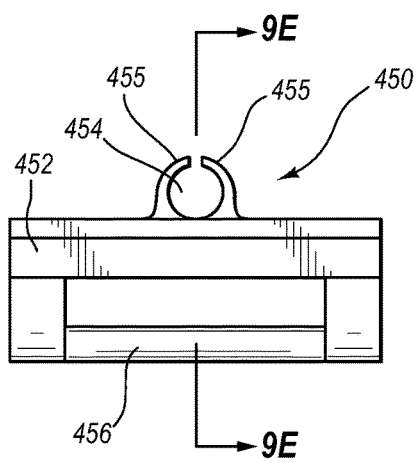
Figure 9E:
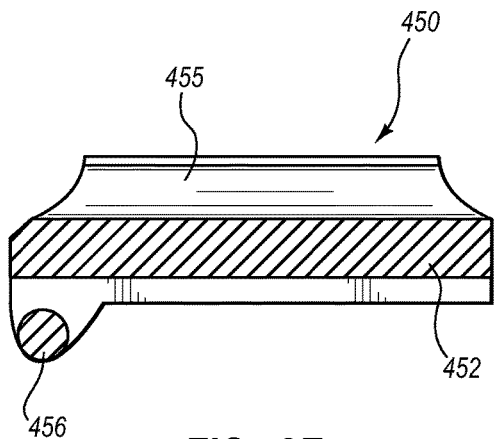

As shown in FIGS. 7A and 7B, in the present embodiment the probe 18 includes on its head portion 18A a connector 470 to which the needle guide can removably attach. The connector 470, which itself can be removably or permanently attached to the probe 18, includes a cavity 472 for receiving the connector 456 of the needle guide base 452, and a support arm 474 proximally extending at an acute angle from the probe surface. The probe 18 further includes a receiver array 480, which includes a second engagement feature, configured here as a plurality of spaced apart bars 482 with which the needle guide hook 462 can engage, as shown in FIG. 8F, for example. Specifically, FIG. 8F shows the needle guide 450 attached to the probe 18 via engagement of its connector 456 with the cavity 472 of the probe connector 470. The hook 462 of the needle guide flexible extension 460 is shown engaged with one of the hook receiving bars 482 of the receiver array 480, thus creating an attachment between the first engagement feature of the needle guide, i.e., the hook 462, and the second engagement feature of the probe, i.e., one of the bars 482.

So configured, the needle channel 454 of the needle guide is oriented to define a needle insertion angle $\theta$ with the probe longitudinal axis 380. Note that the extension 460 is configured to be flexible enough to allow for the bending thereof as shown in FIG. 8F. The support arm 474 in the current embodiment is resilient while also providing the needed rigidity for the needle guide base 452 so as to maintain the needle channel 454 in a substantially fixed location after the angle of the needle guide 450 has been selected and set. Additionally, the stability rails 458 straddle the support arm 474 to prevent undesired twisting or torsion of the needle guide 450 during use.

Should it be desired to change the needle insertion angle defined by the needle channel 454, the hook 462 can be manually moved to engage another of the bars 482 of the probe receiver array 480. This in turn alters the needle insertion angle and the depth to which the needle will be inserted into the patient body by the clinician. Generally, in the present embodiment movement of the hook 462 to more proximal bars 482 lessens the needle insertion angle, which in turn enables the needle to penetrate to a relatively deeper target area in the patient body. Of course, the needle guide system can be configured such that a different relationship exists between movement of the needle guide components and the needle insertion angle. Indeed, in one embodiment the adjustable engagement feature can be included on the needle guide itself instead of on the probe, as is the case with the embodiment described here.

FIGS. 9A-9E depict a variation of the needle guide 450, wherein the free end 460A of the flexible extension 460 serves as a first engagement feature of the needle guide in contrast to the hook of the previous embodiment, and wherein a receiver array 580 on the probe 18 includes a second engagement feature implemented as a plurality of slots 582 instead of the bars of the previous embodiment. Further, the needle guide 450 shown in FIGS. 9A-9E is designed for use with a probe connector that includes no support arm, such as the support arm 474 shown in FIGS. 7A-8F. Instead, the flexible extension 460 in the present embodiment is configured so as to be more rigid, relative to the flexible extension of the embodiment depicted in FIGS. 7A-8F, thus enabling it to bend to engage the receiver array 580 while maintaining the needle guide base 452 at a desired position.

Figure 10A:
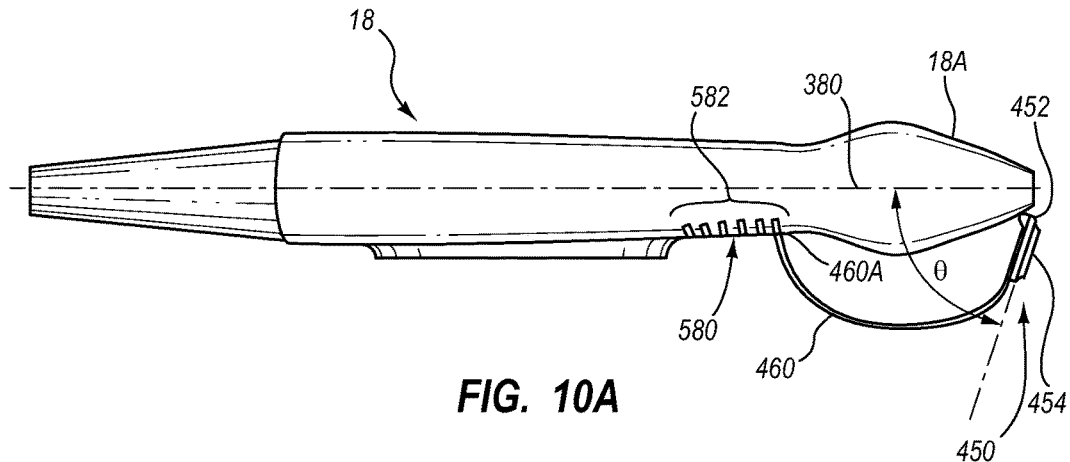
Figure 10B:
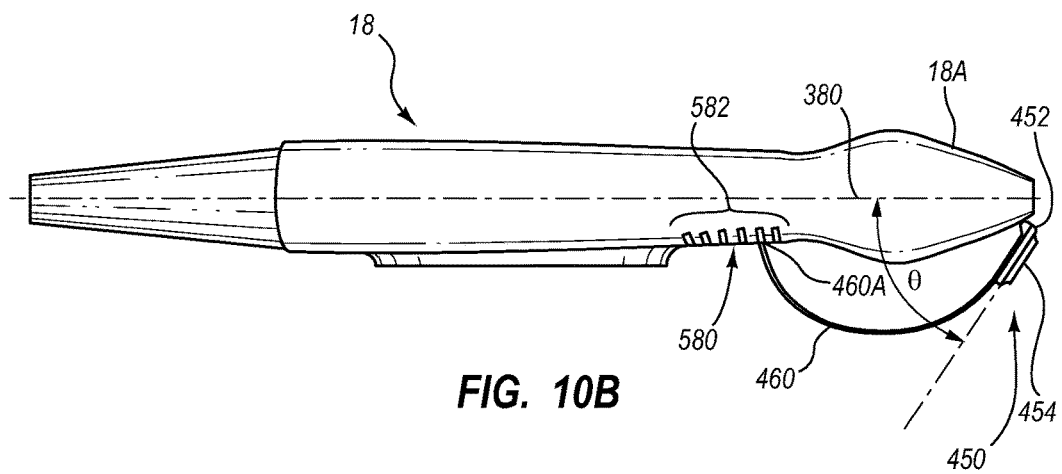
Figure 10C:
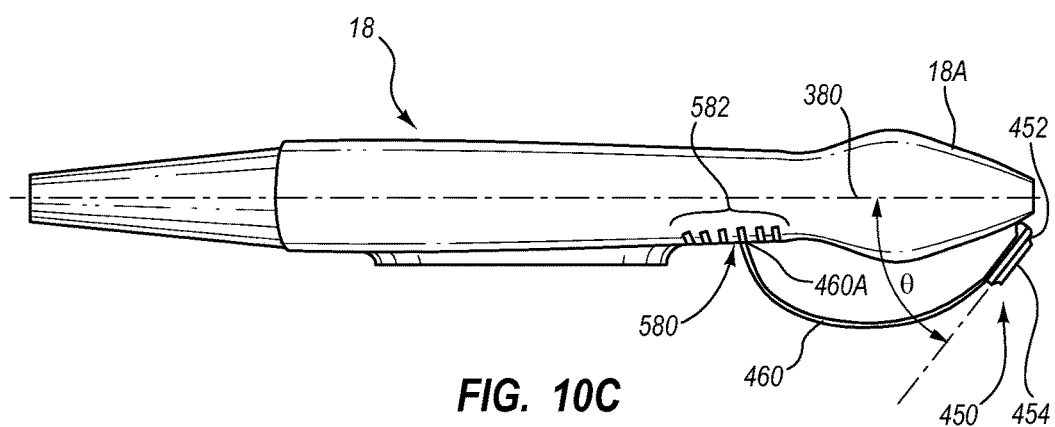
Figure 10D:
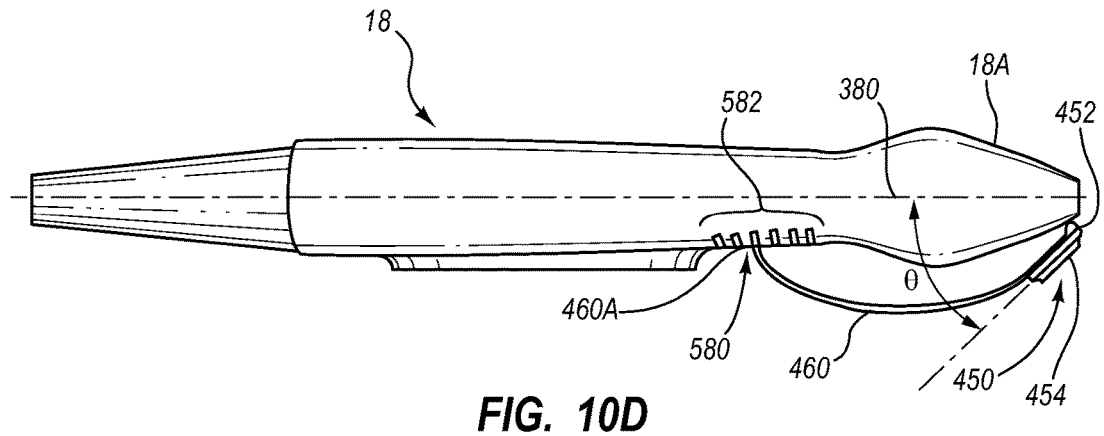
Figure 10E:
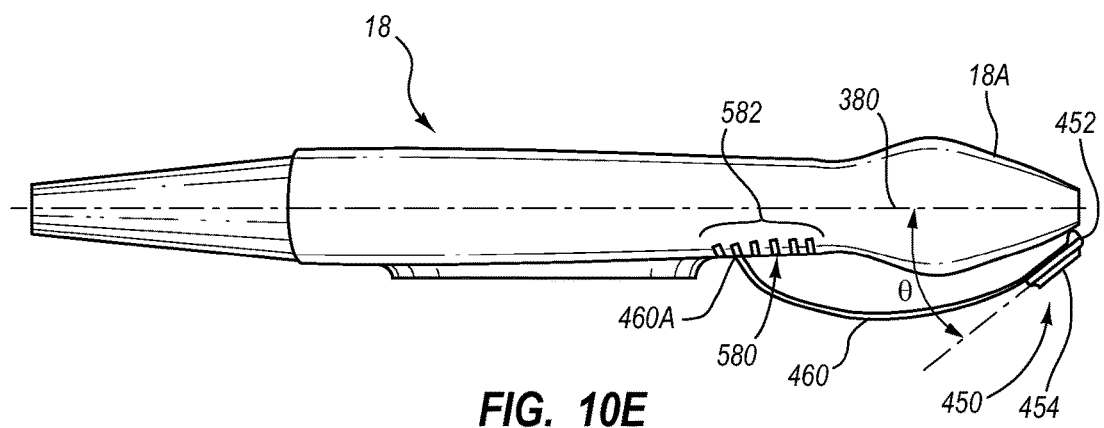
Figure 10F:
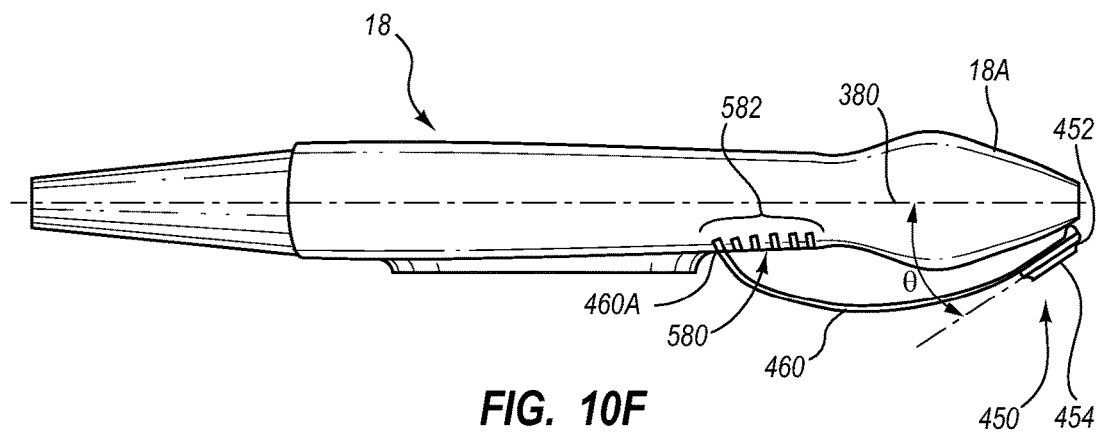

In greater detail, FIGS. 10A-10F show the manner of engagement of the needle guide 450 with the probe 18, according to the first and second engagement features just described above in connection with FIGS. 9A-9E. Note that in FIGS. 10A-10F, the probe connector for attachment of the needle guide has been removed for clarity. In particular, FIG. 10A shows the flexible extension 460 positioned such that the free end 460A thereof is received into the distal-most slot 582 of the probe receiver array 580. This causes the needle guide base 452 and the needle channel 454 disposed thereon to be positioned such that the needle channel defines a relatively large needle insertion angle θ with respect to the probe longitudinal axis 380, which corresponds to inserting a needle in a relatively superficial target area of the patient body located proximate the skin surface thereof.

FIGS. 10B-10F show that as the flexible extension free end 460A of the needle guide 450 is inserted into progressively more proximal slots 582 of the probe receiver array 580, the needle insertion angle θ is reduced, which corresponds to directing the needle to progressively deeper target areas of the patient body. As such, the slots 582 and needle guide 450 can be configured so as to position the needle channel 454 to define predetermined needle insertion angles. In one embodiment, for example, the needle guide system as described in connection with FIGS. 9A-10F can define needle insertion angles ranging from about three degrees to about 43 degrees, though it is appreciated that a variety of possible angles can be achieved. It is noted that the first and second engagement features of the needle guide and probe that are used to interconnect the two can vary from what is described herein, as appreciated by one skilled in the art.

Figure 11A:
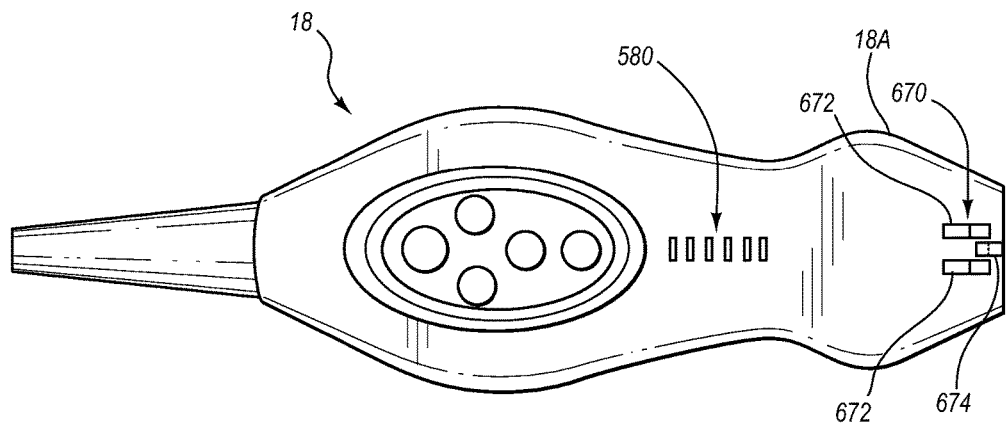
FIGS. 11A-11D show additional details of a needle guide system according to one embodiment.
Figure 11B:
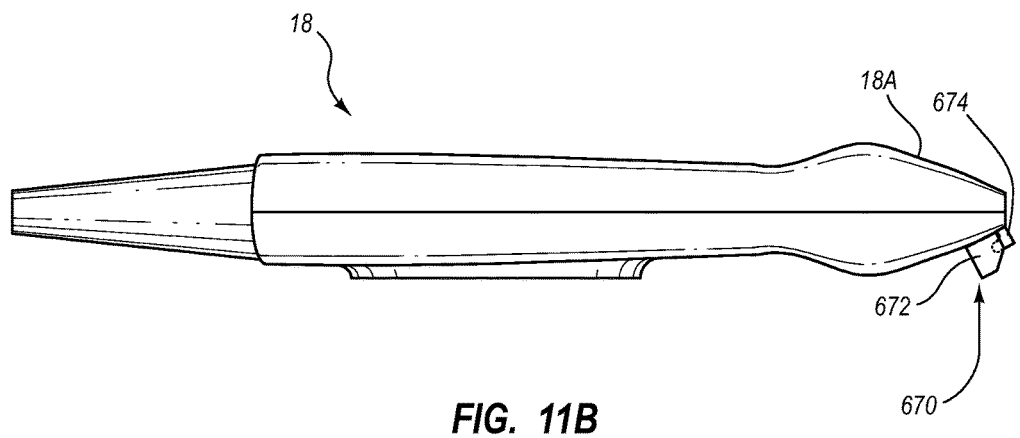
Figure 11C:
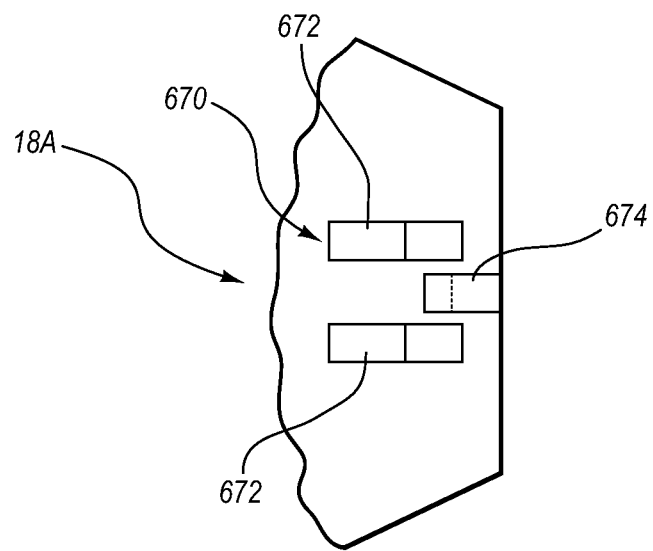
Figure 11D:
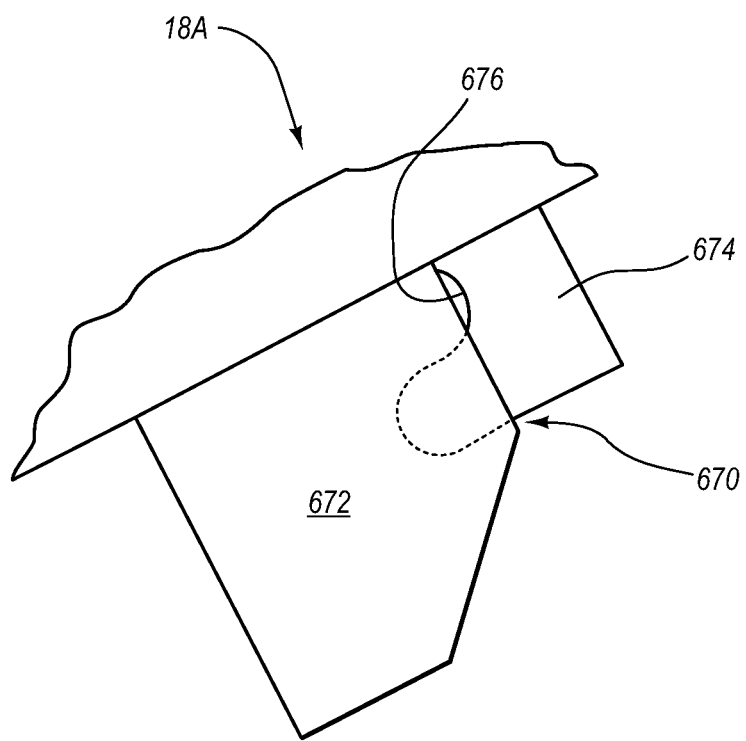

FIGS. 11A-11D depict one possible connector 670 for the probe head portion 18A for engaging a needle guide, according to one embodiment. In particular, the connector 670 includes two outer fins 672 in between which an inner fin 674 is positioned. As best seen in FIG. 11D, a recess 676 is included on the inner fin 674, and the outer fins 672, the inner fin 674, or all the fins include a resilient material so as to enable deformation thereof so as to facilitate insertion into the recess of a connector portion of the needle guide, such as the connector 456 of the needle guide 450 described in the embodiment associated with FIGS. 7A-8F, for example. In one embodiment, only the inner fin is resilient, while the outer fins are substantially rigid. It should therefore be appreciated that the manner of attachment between the needle guide and the probe can include any one of a number of possible designs. Also, it is appreciated that the needle channel can be defined in any one of a number of ways, in addition to the lips explicitly shown and described herein.

Figure 12:
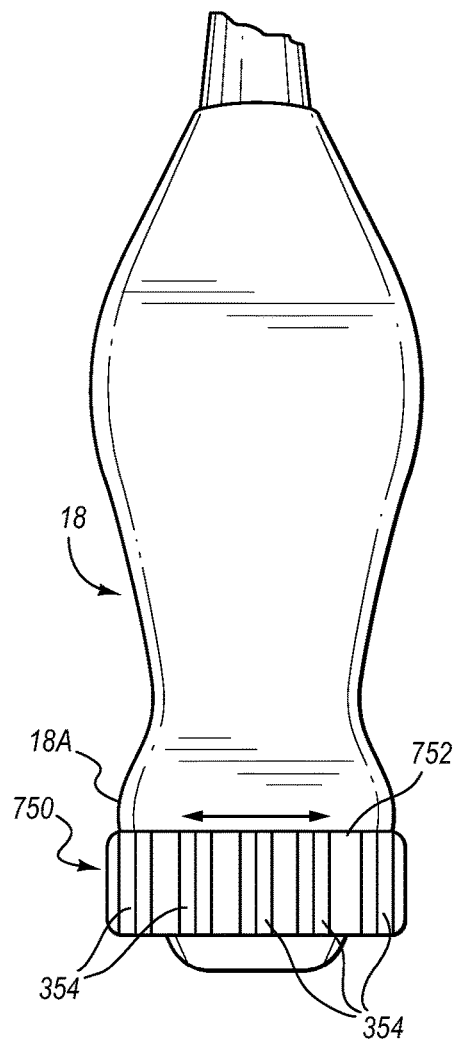
FIG. 12 is a top view of an adjustable needle guide system according to one another embodiment.
Figure 13:
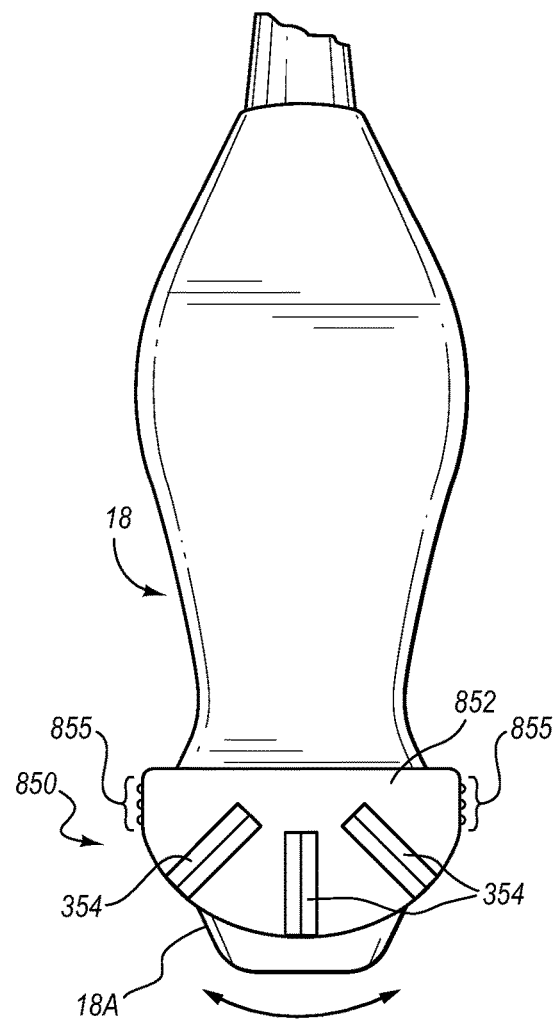
FIG. 13 is a top view of an adjustable needle guide system according to yet another embodiment.

FIGS. 12 and 13 depict yet other needle guide embodiments. In FIG. 12, a linear needle guide 750 is shown, including a top surface 752 on which are disposed a plurality of needle channels 354 that are each aligned to define differing needle insertion angles. A particular needle channel can be selected for use by laterally sliding the needle guide 750 as shown in FIG. 12. In FIG. 13, a semi-circular needle guide 850 is shown, including a top surface 852 on which a plurality of needle channels 354 are disposed in a fan pattern, each needle channel defining a different needle insertion angle. Finger grips 855 can be included on the body of the needle guide 850 to assist with movement of thereof to position a desired needle channel for use. These embodiments are therefore illustrative of the many different needle guide configurations possible.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A needle guide system, comprising:
an ultrasonic probe configured for imaging portions of a patient's body;
a first guide connector extending outwardly from a first surface of the ultrasonic probe, the first guide connector including a first mounting surface that is longest from end to end in a first direction and a second mounting surface that defines two stability extensions extending out from two opposite sides of the first mounting surface in a second direction orthogonal to the first direction, the two stability extensions spanning less than a full length of the first mounting surface from end to end in the first direction; and
a needle guide removably mountable to the first guide connector, the needle guide including a first cavity shaped to receive the first mounting surface, a second cavity which crosses the first cavity and includes notches in two opposite sides of the needle guide for receiving the two stability extensions, and a first channel disposed on a top surface of the needle guide opposite the first cavity, the first channel angled at a first angle with respect to a longitudinal axis of the ultrasonic probe and configured to guide a needle to a targeted depth in the patient's body, wherein two ridges extend along top edges of the two opposite sides of the needle guide from end to end and form a portion of the top surface, each of the two ridges being unbroken along its length.

* * * * *